United States Patent [19]

Zikakis

[11] 4,246,341
[45] Jan. 20, 1981

[54] PROCESS FOR DETECTING ENZYMATICALLY ACTIVE XANTHINE OXIDASE

[75] Inventor: John P. Zikakis, Townsend, Del.

[73] Assignee: University of Delaware, Newark, Del.

[21] Appl. No.: 14,337

[22] Filed: Feb. 23, 1979

Related U.S. Application Data

[62] Division of Ser. No. 806,736, Jun. 15, 1977, Pat. No. 4,172,763.

[51] Int. Cl.$^3$ ............................................. C12Q 1/26
[52] U.S. Cl. ..................................................... 435/25
[58] Field of Search .................... 435/25; 195/103.5 R

[56] References Cited

PUBLICATIONS

Anderson et al., *Science*, 120, 956, (1954).
Davis, *Ann. N.Y. Acad. Sci.*, 121, 404–427, (1964).
Ornstein, *Ann. N.Y. Acad. Sci.*, 121, 321–348, (1964).
Feinstein et al., *Analytical Biochemistry*, 56, 353–360, (1973).
Zittle et al., *J. of Dairy Science*, vol. XXXIX, No. 5, 522–527, (1956).
Owen, *Methods in Enzymology, vol. XVIII, Part B*, Academic Press, New York, Colowick, Editor, (1971), 590–592.

Primary Examiner—Alvin E. Tanenholtz

[57] ABSTRACT

A process for detecting and visualizing enzymatically active xanthine oxidase which comprises first analysis by discontinuous polyarcylamide gel electrophoresis and then staining the polyacrylamide gel containing xanthine oxidase using neotetrazolium chloride.

1 Claim, No Drawings

PROCESS FOR DETECTING ENZYMATICALLY ACTIVE XANTHINE OXIDASE

This application is a division of application Ser. No. 806,736 filed June 15, 1977 now U.S. Pat. No. 4,172,763.

FIELD OF THE INVENTION

This invention relates to an improved method for detecting and visualizing enzymatically active xanthine oxidase. Highly purified xanthine oxidase (referred to herein as XO) is needed in research and in a variety of industrial, clinical, and pharmaceutical applications.

PRIOR ART

Bovine milk xanthine oxidase (xanthine: oxygen oxidoreductase; E.C. 1.2.3.2.) is a conjugated iron-sulfur molybdenum flavoprotein widely distributed in animals, plants, and microorganisms where it has a role in purine catabolism. In many animals, including primates, XO is found in the liver, kidney, blood, intestinal mucosa and milk (Li and Vallee, In Modern Nutrition in Health and Disease: Dietotherapy, 5th Ed. Lea and Febiger, Philadelphia, Pa., pp. 372-399, 1973; Zikakis et al, J. Food Sci. 41:1408-1412, 1976). It catalyzes uric acid production from hypoxanthine and xanthine in terminal purine catabolism.

Most of the XO in cow's milk is closely associated with the milk fat globule membrane (MFGM) (Morton, Biochem J. 57:231-237, 1954). The MFGM has a protenaceous surface that interfaces with the milk plasma phase on the exterior and the globule lipids on the interior (Brunner, In Fundamentals of Dairy Chemistry, 2nd Ed. AVI Publishing Co., Westport, Conn., pp. 474-602, 1974).

Ball in 1939 (J. Biol. Chem. 128:51-67) was the first to isolate and partially purify XO from cow's milk by treating buttermilk with pancreatin. From 1955 to the recent past, numerous purification methods for cow's milk XO have been described. Pancreatin has been used in XO purification to degrade casein micelles to lower molecular weight components so that they may be eluted behind XO in subsequent chromatographic fractionations. However, pancreatin is not specific for casein degradation, and has a proteolytic effect on all proteins (Nelson and Handler, J. Biol. Chem. 243:5368-73, 1968). Avis et al., (J. Chem. Soc. (London) pp. 1100-1105, 1955) managed to crystallize XO in the presence of ethanol giving a protein/flavin ratio (a most important purity index for XO) of 5.0-5.2. However, the yield was poor and the specific activity of the product varied widely.

In 1964, Gilbert and Bergel (Biochem. J. 90:350-353) published a method which improved the yield but the product was less pure ($E_{280}/E_{450}$ ranged from 5.4-6.0) than that of Avis et al., 1955. Their method included pancreatin digestion of the buttermilk, treatment with butanol, and the addition of EDTA and sodium salicylate. In 1968 Nelson and Handler prepared milk XO by a non-proteolytic method (i.e., without pancreatin digestion). They concluded that their preparation was homogeneous, with a $E_{280}/E_{450}$ ratio of 5.1-5.3. Hart et al., (Biochem. J. 116:851-863, 1970) and Nelson and Handler (1968) have indicated that purified XO differs according to the purification method, and that proteolysis adversely affects the enzyme. Waud et al. (Arch. Biochem. Biophys. 169:695-701, 1975), and Nagler and Vartanyan (Biochem. Biophys. Acta 427:78-90, 1976) demonstrated that purification procedures employing pancreatin yield XO and sub-units with lower molecular weight, and that the XO migrates faster on polyacrylamide gel electrophoresis than XO prepared by a non-proteolytic treatment. Furthermore, Nathans and Hade (Biochem. Biophys. Res. Comm. 66:108-114, 1975) showed that XO isolated in the presence of pancreatin copurifies with proteases from pancreatin. The non-proteolytic procedure of Waud et al., (1975) which comprises butanol extraction, ammonium sulfate precipitation, and chromatography is the best available method. The final product never has a $E_{280}/E_{450}$ ratio better than 4.8 and the yield is 10%.

In summary, prior art teaches an incubation of milk buffered with Sodium Salicylate and EDTA; digestion with pancreatin, or extraction with butanol, washing with an ionic detergent; precipitation of casein with ammonium sulfate; further removal of casein by treatment with ammonium sulfate, and finally purifying on one or two chromatographic columns.

The objective of this invention is to obtain a purer XO than produced by prior art by operating under conditions that improve the final product. The invention features the use of a mild non-ionic detergent, maintaining at low temperature to remove more casein, and the use of ultrafiltration and multiple chromatographic columns to concentrate the XO and remove non-XO proteins with lower or higher molecular weights.

SUMMARY OF THE INVENTION

This invention consists of an improved method for the isolation and purification of XO from bovine raw milk. To assure good yield, the starting milk is assayed for XO activity before using it. As a rule, good yield is expected when the activity of starting fresh raw milk (which is maintained immediately after milking at 38° C. and assayed within 60 min.) is above 60 $\mu$l $O_2$/ml/hr. or above 140 $\mu$l $O_2$/ml/hr. for raw milk kept at 4' C. for 1-12 hrs. after milking. Sodium salicylate and EDTA are added as enzyme protectors. The mixture is diluted 1:1 with potassium phosphate buffer and incubated at 40° to 45° C. for 2 hours with continuous mixing. After 105 min. of incubation, 1% by volume of Triton X-100 or a similar non-ionic detergent is added and the mixture is allowed to incubate for 15 min. The use of a non-ionic detergent facilitates the separation of the XO from MFGM without adding ionic salts or degrading the enzyme.

The mixture is cooled to 4° C. and all subsequent steps are carried at that temperature. Solid ammonium sulfate is added (200 gm/liter) to the mixture, which is stirred for 15 min., and then centrifuged at 12,225 g for 20 min. To the resulting yellow supernatant liquid, which contained the enzyme, solid ammonium sulfate is added (70 gm/liter), stirred for 15 min., and centrifuged at 12,225 g for 20 min. The red-brown percipitate is dissolved in a minimal volume of 0.1 M Tris*/$CaCL_2$ buffer (pH 7.0) and stored at freezing or below (e.g. −20° C.) for from 0.5 to 7.0 days. Prior art does not call for storage at that temperature, but this step precipitates caseins which are the commonest non-XO proteins in milk.

* Tris(hydroxymethyl)aminomethane

The frozen preparation is thawed and centrifuged at 12,225 g for 20 min. The active enzyme retained in the supernatant liquid is concentrated on a XM50 microfilter and applied on a Sephadex G-75 column. The eluted fractions are analyzed spectrophotemetrically at 280 and 450 nm and catalytic activity is measured at 295 nm. Fractions showing activity are pooled, concentrated, and reanalyzed as above. The concentrated sample is applied on a Sephacryl S-200 superfine or on a Sephadex G-200 column. The eluted fractions are analyzed for absorption and activity, active fractions pooled, concentrated as above, and passed through a Sepharose 6B type column. All eluted fractions are tested as above; fractions with activity are pooled, concentrated as above, and desalted by passage through a Sephadex G-75 column. Finally, the active fractions from this column are pooled, concentrated, and applied on either a DEAE Sephadex A-50 or on DEAE Sepharose CL-6B anionic exchange column and eluted in a continuous linear salt gradient from 0.005 to 0.1 M pyrophosphate buffer, pH 8.6.

The sizing of the ultrafiltration membrane and the order of use of the chromatographic colums are both important. According to the majority of studies, the M.W. of XO is about 300,000 daltons (Waud et al., 1975; Nagler and Vartanyan, (Biokhimiya 38:561–567, 1973—translated from Russian) with two subunits of about 150,000 daltons (Nathans and Hade, 1975; Nagler and Vartanyan, 1976). In turn, this subunit of XO may be a dimer of 80,000–85,000 daltons. This is supported by the fact that the ultrafiltrate of XO preparations passed through an Amicon XM-100A membrane (with a nominal cutoff of 100,000 daltons) contained active XO (Nathans and Hade, 1975; Biasotto and Zikakis (J. Dairy Sci. 58:1238, 1975). This suggests that XO may be a tetramer which may undergo dissociation and reassociation. Thus, to avoid the loss of monomers of XO and increase the yield, the Amicon XM-50 membrane (nominal cutoff 50,000 daltons) was used in this procedure. This membrane retains molecules with M.W. above 50,000 and allows all others to pass through. The first column used is Sephadex G-75 which retains salts and light particles and allows heavy particles (including XO) to come out first. Both Sepharyl S-200 and Sepharose 6B columns separate proteins in the preparation according to molecular size. Before the final purification step through DEAE Sephadex A-50 (or through DEAE Sepharose CL-6B) anionic exchange column, the XO preparation is passed again through Sephadex G-75 to remove all salts (this is a necessary step; otherwise, XO will not bind to the anionic exchange column).

The final enzyme preparation has on the average a constant ratio of $E_{280}/E_{450}$ of 4.1, and one symmetric peak by gel chromatography. Analysis on polyacrylamide disc gel electrophoresis shows a single band. The average yield of the final product is 21%, which is about 110% higher than that obtained using the best available prior art; which also produces a less pure enzyme. Analyses on polyacrylamide disc gel electrophoresis reveal that the commercial XO migrates faster than does XO prepared by this method. Also, commercial XO contains 7–14 bands depending on the batch. Using neotetrazolium chloride dye, it was found only one band in the commercially prepared XO contained activity, while the rest were impurities.

UTILITY OF INVENTION

Milk xanthine oxidase is of great interest because of its complexity and catalytic versatility. The enzyme has low specificity for substrates and electron acceptors. It catalyses the oxidation of many purines, pteridines, aldehydes, and other heterocyclic compounds by a number of electron acceptors such as oxygen, NADH, dyes, ferricyanides, and cytochrome C (Avis et al., J. Chem. Soc. (London) Part I: 1212–1219, 1956; corran et al., Biochem. J. 33:1694–1706, 1939; Murrey et al., J. Biol. Chem. 241:4798–4801, 1966). The presence of XO in excess or its absence, inhibition, or stimulation, reflects on the biochemistry of normal or abnormal cellular activity (Wyngaarden and Kelley, In the Metabolic Basis of Inherited Disease, 3rd Ed., McGraw-Hill Book Co., New York, N.Y., 1972). Although the primary pathway of uric acid production is known, the metabolic importance of XO is not fully understood. Recently it has been theorized that XO in bovine milk is a factor in the development of atherosclerosis in humans (Oster, Amer. J. Clin. Res. 2:30–35, 1971; In Myocardiology Vol. 1, pp. 803–813, University Park Press, Baltimore, Md., 1972; Ross et al., Proc. Soc. Exp. Biol. Med. 144:523–527, 1973). the production of high purity XO will stimulate research in the above fields and may lead to clinical and industrial applications. A major producer of XO has recently discontinued production because of difficulty in producing acceptable XO. A process better than the prior art is needed.

The following example describes in greater detail the preferred process steps used in carrying out the process of this invention.

EXAMPLE

1. To one liter of fresh raw milk (from the University of Delaware Guernsey herd) 10 ml of 200 mM sodium salicylate and 0.1 gm EDTA added and mixed. Sodium salicylate stabilizes XO while EDTA chelates heavy metal contaminants. One liter of 0.2 M potassium phosphate buffer (pH 7.8), containing 8 mM sodium salicylate and 4 mM cysteine-HCL, was added to the mixture and mixed. The final concentration of solutes in this 2 liter mixture was 5 mM sodium salicylate, 0.005% EDTA, 0.1 M $K_2HPO_4$, and 2 mM cysteine-HCL. The pH of the mixture ranged between 7.8 to 7.9.

2. The mixture was incubated while stirring at 40 to 45° C. for 2 hours. After 105 minutes incubation, 1% (V/V) Triton X-100 was added to the mixture and the mixture allowed to continue incubation for 15 minutes. Triton X-100 is a mild non-ionic detergent which is effective in dissolving the MFGM. Triton X-100 is a substitute for the much harsher lipolytic enzymes (which may adversely effect the purity of XO) and butanol (which is a denaturant and a substance difficult to work with) presently used in other methods. At the end of the two-hour incubation, the mixture was cooled to 4° C. and, unless stated otherwise, all subsequent steps of the method were carried out at this temperature.

3. 400 gm of the solid ammonium sulfate (20% W/V) was added to the mixture with stirring. The suspension was stirred for 15 minutes and then centrifuged at 12,225 g for 20 minutes in an International Refrigerated Centrifuged (Model B-20). Three distinct layers were formed after centrifugation. The upper layer (the milk-fat) and the white precipitate (the caseins) at the bottom of the tubes were devoid of XO activity and were discarded. The supernatant liquid was passed through glass wool into a graduated cylinder. The filtrate was an opalescent yellow fluid which contained all the XO activity.

4. The concentration of ammonium sulfate in the filtered supernatant liquid was adjusted from 20% to 27% with solid ammonium sulfate, the mixture stirred for 15 minutes and centrifuged at 12,225 g for 20 min. The resultant brownish-red precipitate was dissolved in 10 to 15 ml of 0.1 M Tris-HCl buffer (pH 7.0) containing 2 mM sodium salicylate and 0.07 M $CaCl_2$ and stored for at least 15 hours at $-20°$ C. The objective of this step was the precipitation of caseins (Ball, 1939). About 80% of the total protein in cow's milk is casein which precipitates over the range of 20 to 26.4% (W/V) ammonium sulfate (McKenzie, In Milk Protein Chemistry and Molecular Biology, Vol. 2 pp. 87–114, Acad. Press, New York, N.Y., 1971). This fractionation range is close to the 27% W/V ammonium sulfate used to precipitate XO in this procedure. Therefore, the inclusion of some caseins in the above precipitations is unavoidable.

5. Upon thawing the mixture to 22° C., it yielded a course white precipitate of caseins. Upon centrifugation at 12,225 g and 4° C. for 20 min., the mixture yielded a reddish-brown supernatant liquid and a slightly brown precipitate. The precipitate was redissolved in 0.1 M Tris/$CaCl_2$ buffer and recentrifuged. The supernatant liquid from both centrifugations was combined and showed high activity of XO, while the white precipitate of caseins had negligible activity. It was found that the longer the preparation was frozen, the more caseins can be removed. Maximum casein precipitation occurs after about 3 to 4 weeks of storage at $-20°$ C. Therefore, the time of cold storage is a function of economics and the desired purity. The precipitation of casein is very slow after 7 days and some decomposition of XO will occur, even at $-20°$ C. Storage of most batches were from 15 hours to 1 week, which is usually a satisfactory operating range.

6. The active reddish-brown supernatant obtained in step 5 was concentrated to 5 ml on an Amicon ultrafiltration system using a XM50 membrane designed to retain molecules of 50,000 daltons and greater. This concentrate was then applied on a Sephadex G-75 superfine column (1.5×125 cm), which has been equilibrated with 0.1 M pyrophosphate buffer pH 7.1, and the column was eluted with the same buffer. The purpose of this chromatographic step was to desalt (remove the ammonium sulfate) and remove low molecular weight (<75,000 daltons) impurities from the sample. All fractions were analyzed individually at 280 nm for protein and at 450 nm for flavin adenine dinucleotide (FAD) on either a Beckman DB or a Gilford Model 250 spectrophotometer. From this point on, the enzyme activity in each fraction was measured spectrophotometrically at 295 nm and 23.5° C. Fractions with activity were pooled and concentrated by ultrafiltration as above to 5 ml. The pooled sample was analyzed for activity, absorption spectra, total protein, and electrophoretic behavior.

7. The pooled, concentrated sample from step 6 was applied on a Sephacryl S-200 superfine or on a Sephadex G-200 column (2.5×100 cm) equilibrated with 0.1 M pyrophosphate buffer 7.1, and the column was eluted with the same buffer. All fractions were analyzed as above. Fractions with no activity were discarded. The remaining fractions showed increases in purity as judged by the protein flavin ration (PFR), activity-flavin ratio (AFR), activity-protein ratio (APR), and electrophoresis.

8. The fractions from the Sephacryl S-200 (or the Sephadex G-200) (step 7) showing XO activity at 295 nm and flavin at 450 nm, were pooled, concentrated, and applied on a Sepharose 6B column (2.5×100 cm) equilibrated and eluted with 0.1 M phrophosphate buffer pH 7.1. Following analyses of eluted fractions, those with XO activity were pooled and concentrated to about 3 ml by ultrafiltration using a XM50 membrane.

9. The concentrated sample of step 8 was desalted by passing it through a Sephadex G-75 column (0.9×60 cm) equilibrated and eluted with a 0.005 M sodium pyrophosphate buffer pH 8.6. Fractions containing the enzyme were pooled and concentrated on a XM50 membrane.

10. The concentrated sample was applied on a DEAE Sephadex 50-A (or on a DEAE Sepharose CL-6B) anionic exchange column (1.6×20 cm) which was equilibrated with 0.005 M sodium pyrophosphate buffer pH 8.6. Initial elution of the column was with the 0.005 M phosphate buffer. At this pH and salt concentration, XO is effectively bound to the exchanger as was apparent from the appearance of a dark brown band in the upper 2 to 4 cm of the column and its failure to elute in 0.005 M salt. Elution of XO from the column was accomplished on a linear continuous salt gradient from 0.005 M to 0.1 M sodium pyrophosphate pH 8.6. Typical data obtained at various stages of XO preparation are listed in Table 1.

TABLE 1

TYPICAL DATA OBTAINED AT VARIOUS STAGES OF XANTHINE OXIDASE PURIFICATION FROM GUERNSEY MILK

| PROCEDURE | TOTAL VOLUME (ml) | ACTIVITY (1 UNITS/ ml) | PROTEIN (mg/ml) | SPEC. ACTIVITY | PFR[1] | PURIFICATION |
|---|---|---|---|---|---|---|
| WHOLE MILK | 1000 | 0.034* | 22.66 | 0.0015 | ** | 0 |
| AFTER BUFFER ADDITION | 2000 | 0.017* | 11.32 | 0.0015 | ** | 0 |
| AFTER DIGESTION | 2000 | 0.104* | 12.60 | 0.0083 | ** | 5.6 |
| 20% CUT | 1862 | 0.115* | 2.26 | 0.051 | ** | 34.0 |
| 7% CUT | 6.5 | 31.89 | 18.90 | 1.687 | 24.5 | 1125.0 |
| G-75 | 6.0 | 18.43 | 18.60 | 0.991 | 16.0 | 660.6 |
| SEPHACRYL S-200 OR SEPHADEX G-200 | 6.0 | 17.71 | 12.40 | 1.428 | 10.0 | 952.0 |
| SEPHAROSE 6B | 3.5 | 20.71 | 12.40 | 1.670 | 8.0 | 1113.3 |

TABLE 1-continued
TYPICAL DATA OBTAINED AT VARIOUS STAGES OF XANTHINE OXIDASE PURIFICATION FROM GUERNSEY MILK

| PROCEDURE | TOTAL VOLUME (ml) | ACTIVITY (1 UNITS/ml) | PROTEIN (mg/ml) | SPEC. ACTIVITY | PFR[1] | PURIFICATION |
|---|---|---|---|---|---|---|
| DEAE+ | 3.5 | 12.20 | 1.70 | 7.176 | 4.1 | 4784.3 |

[1]PROTEIN FLAVIN RATIO.
*ACTIVITY OF SAMPLES PRIOR TO THE 7% AMMONIUM SULFATE CUT WAS DETERMINED POLAROGRAPHICALLY.
**THE PFR COULD NOT BE CALCULATED FOR SAMPLES PRIOR TO THE 7% AMMONIUM SULFATE CUT DUE TO THE TURBIDITY OF THE SAMPLE.

The most sensitive indicator of XO purity is the PFR ($E_{280}/E_{450}$) value (Hart et al., 1970). A decrease in the concentration of non-XO protein (at 280 nm) and a simultaneous increase in the concentration of XO (at 450 nm) should give an increasingly lower $E_{280}/E_{450}$ ratio. Thus, the lower the PFR value, the higher the purity of the preparation. PFR values obtained by various methods are: 6.2 (Corran et al., 1939), 6.2 (Morell. Biochem. J. 51:657-666, 1952), 5.0 (Avis et al., 1955), 5.4 (Gilbert and Bergel, 1964), 5.1 (Nelson and Handler, 1968), 5.2 (Nagler and Vartanyan, 1973), and 4.8 (Waud et al., 1975).

The enzyme purified by this method had on the average a constant ratio of $E_{280}/E_{450}$ of 4.1 (the lowest PFR value ever reported), one symmetric peak by ion-exchange chromatography, and its behavior on polyacrylamide disc gel electrophoresis showed a single active band. Comparative analyses of commercially available XO, and of XO as prepared by this method, revealed that commercial XO migrates faster in electrophoresis than does XO by this method. Furthermore, the commercial enzyme contained 7-14 bands depending on the batch. A rapid method was devised to localize activity of XO directly on electrophoretic gels using neotetrazolium chloride dye. This method involved discontinuous polyacrylamide gel electrophoresis.

The discontinuous polyacrylamide gel electrophoresis was performed using a Buchler 18 tube Polyanalyst according to the methods of Ornstein (Ann. N.Y. Acad. Sci. 121:321, 1964) and Davis (Ann. N.Y. Acad. Sci. 121: 321 and 404, 1964). Pore sizes in the gels were based on the use of 3.5% acrylamide in the sample and spacer gels and 10% acrylamide in the separating gel. Gels were run at basic pH of 8.3 using Tris/Glycine buffer at 2.5 to 3.0 milliamps/tube. The gel was stained for the presence of active XO bands with neotetrazolium chloride solution [250 mg of neotetrazolium chloride was dissolved in 1 liter of 10 mM xanthine (in 25 mM NaOH) and the pH adjusted to 8.3. The solution was light brown]. The gel containing XO was not fixed in trichloroacetic acid but were immersed for 1 to 10 hours in the dye mixture. When the gels contained enzymatically active XO, the process resulted in the formation of a purple color band. Detection of active XO by neotetraxolium chloride involves the direct transfer of electrons from the substrate (xanthine) first to the flavin adenine dinucleotide moiety of the enzyme and then to neotetrazolium chloride. As a result of this electron transfer, the purple color precipitate formazan is formed.

Gels stained as above were removed from the stain solution and immersed in distilled water for photography. The colored bands in the gel remained visible at 4° C. for up to 3 months, but faint out at room temperature in 2 to 6 days, depending on the activity of the enzyme stained. Using this technique, commercially prepared XO was analyzed electrophoretically and found that only one band (out of 7-14) contained XO activity, the rest were impurities.

The PFR value of the final XO preparation ranged from 2.7 to 4.8 and averaged 4.1. The yield of the method ranges from 18-26% and average 21%. Therefore, this method produces XO which is on the average about 20% purer (about 4800 fold purified) and yields about 110% more XO than the best available method in literature (Waud et al., 1975).

More highly purified XO with PFR value approaching 2.0 can be obtained by this method using additional treatment in columns, but the yield is smaller and the cost of the product is greater.

It is apparent that changes and modifications may be made without departing from the invention in its broader aspects. The aim of the appended claims, therefore, is to cover all such changes and modifications as fall within the true spirit and scope of the invention.

I claim:

1. A process for detecting and visualizing enzymatically active xanthine oxidase which comprises first analyzing xanthine oxidase containing liquid by discontinuous polyacrylamide gel electrophoresis where pore sizes in the gels are based on the use of 3.5% acrylamide in the separating gel and gels are run in a basic pH of 8.3 using Tris/Glycine buffer at 2.5 to 3.0 milliamps/tube then immersing the gels containing xanthine oxidase for 1 to 10 hours in neotetrazolium chloride and xanthine solution mixture where the active xanthine oxidase reacts with the substrate xanthine transferring its electrons first to flavin adenine dinucleotide moiety of the enzyme and then to neotetrazolium chloride forming a purple color precipitate (formazan) at the site where the active xanthine oxidase is located and visualizing the position of the enzyme in the gel.

* * * * *